United States Patent
Petkov et al.

(10) Patent No.: US 10,957,098 B2
(45) Date of Patent: Mar. 23, 2021

(54) CONSISTENT 3D RENDERING IN MEDICAL IMAGING

(71) Applicant: Siemens Healthcare GmbH, Erlangen (DE)

(72) Inventors: Kaloian Petkov, Lawrenceville, NJ (US); Chen Liu, Vaud (CH); Shun Miao, Bethesda, MD (US); Sandra Sudarsky, Bedminster, NJ (US); Daphne Yu, Yardley, PA (US); Tommaso Mansi, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/789,586

(22) Filed: Feb. 13, 2020

(65) Prior Publication Data
US 2020/0184708 A1    Jun. 11, 2020

Related U.S. Application Data

(62) Division of application No. 15/827,263, filed on Jan. 3, 2018, now Pat. No. 10,607,393.
(Continued)

(51) Int. Cl.
*G06T 15/08* (2011.01)
*G16H 30/20* (2018.01)
(Continued)

(52) U.S. Cl.
CPC .............. *G06T 15/08* (2013.01); *A61B 5/055* (2013.01); *A61B 6/032* (2013.01); *A61B 6/037* (2013.01);
(Continued)

(58) Field of Classification Search
CPC ....... G06T 15/08; G06T 15/06; G06T 15/506; G06T 7/0012; G06T 11/008;
(Continued)

(56) References Cited

U.S. PATENT DOCUMENTS 8,711,144 B2  4/2014  Johnson et al.
9,008,391 B1  4/2015  Solanki et al.
(Continued)

OTHER PUBLICATIONS

Novak et al., Path Regeneration for Interactive Path Tracing, EUROGRAPHICS 2010, 4 pages. Downloaded from https://jannovak.info/publications/PathRegPT/PathRegPT.pdf on Oct. 1, 2020. (Year: 2010).*

(Continued)

*Primary Examiner* — Haixia Du

(57) ABSTRACT

For three-dimensional rendering, a machine-learnt model is trained to generate representation vectors for rendered images formed with different rendering parameter settings. The distances between representation vectors of the images to a reference are used to select the rendered image and corresponding rendering parameters that provides a consistency with the reference. In an additional or different embodiment, optimized pseudo-random sequences are used for physically-based rendering. The random number generator seed is selected to improve the convergence speed of the renderer and to provide higher quality images, such as providing images more rapidly for training compared to using non-optimized seed selection.

6 Claims, 5 Drawing Sheets

Related U.S. Application Data

(60) Provisional application No. 62/469,703, filed on Mar. 10, 2017.

(51) Int. Cl.

| | | |
|---|---|---|
| *G06T 7/00* | (2017.01) | |
| *G16H 30/40* | (2018.01) | |
| *A61B 5/055* | (2006.01) | |
| *A61B 6/03* | (2006.01) | |
| *A61B 8/08* | (2006.01) | |
| *G06K 9/62* | (2006.01) | |
| *G06T 11/00* | (2006.01) | |
| *G06T 15/06* | (2011.01) | |
| *G06T 15/50* | (2011.01) | |
| *G06N 3/08* | (2006.01) | |

(52) U.S. Cl.
CPC ............ *A61B 8/483* (2013.01); *G06K 9/6256* (2013.01); *G06T 7/0012* (2013.01); *G06T 11/008* (2013.01); *G06T 15/06* (2013.01); *G06T 15/506* (2013.01); *G16H 30/20* (2018.01); *G16H 30/40* (2018.01); *G06N 3/08* (2013.01); *G06T 2210/41* (2013.01); *G06T 2211/40* (2013.01)

(58) Field of Classification Search
CPC . G06T 2210/41; G06T 2211/40; G16H 30/20; G16H 30/40; A61B 5/055; A61B 6/32; A61B 8/483; G06K 9/6256; G06N 3/08
See application file for complete search history.

(56) References Cited

U.S. PATENT DOCUMENTS

| | | | |
|---|---|---|---|
| 9,324,022 B2 | 4/2016 | Williams, Jr. et al. | |
| 9,760,690 B1 | 9/2017 | Petkov et al. | |
| 2011/0122135 A1* | 5/2011 | Kim | G06T 1/20 345/426 |
| 2014/0029849 A1 | 1/2014 | Sen et al. | |
| 2014/0119672 A1 | 5/2014 | Ioffe et al. | |
| 2014/0328526 A1 | 11/2014 | Wahrenberg | |
| 2015/0170004 A1 | 6/2015 | Song et al. | |
| 2015/0320507 A1 | 11/2015 | Qiu et al. | |
| 2016/0242740 A1 | 8/2016 | Day | |
| 2017/0116498 A1 | 4/2017 | Raveane et al. | |
| 2018/0234671 A1 | 8/2018 | Yang et al. | |

OTHER PUBLICATIONS

Plis, Sergey M. et al, "Deep learning for neuroimaging: a validation study." (2014), pp. 1-11.

Ku Yan et al, "Deep Learning of Feature Representation With Multiple Instance Learning for Medical Image Analysis"; 2014 International Conference on Acoustics, Speech and Signal Processing (ICASSP), IEEE, 2014.

Lai M., Deep learning for medical image segmentation. arXiv preprint arXiv:1505.02000. May 8, 2015, pp. 1-23.

Li Rongjian et al. "Deep Learning Based Imaging Data Completion for Improved Brain Disease Diagnosis"; Network and Parallel Computin; Lecture Notes in Computer Science; Springer international Publishing, Cham; pp. 305-312.

Plis, Sergey M. et al, "Deep learning for neuroimaging: a validation study." (2014), pp. 1-11.

Sadeghi, et al. "Coherent path tracing." Journal of Graphics, GPU, and Game Tools 14.2 (2009): 33-43.

Soundararajan, Krishna Prasad, and Thomas Schultz. "Learning Probabilistic Transfer Functions: A Comparative Study of Classifiers." Computer Graphics Forum. vol. 34. No. 3. 2015.

Zhang, Jia-Wan, and Ji-Zhou Sun. "Adaptive transfer function design for volume renering by using a general regression neural network [renering read rendering]." Machine Learning and Cybemetics, 2003 International Conference on. vol. 4. IEEE, 2003.

Zheng, Yefeng et al. "3D Deep Learning for Efficient and Robust Landmark Detection in Volumetric Data", in: Int. Conf. on Medical Image Computing and Computer Assisted Interventions, 2015.

Extended European Search Report (EESR) dated Jul. 13, 2018 in corresponding European Application No. 18160956.1.

Annarumma, Mauro, et al. "Deep metric learning for multi-labelled radiographs", arxiv.org, Cornell University Library, Ithaca, NY, Dec. 11, 2017.

Wan, Ji, et al., "Deep Learning for Content-Based Image Retrieval", multimedia, ACM, 2 Penn Plaza, suite 701, NY 10121-0701 USA, Nov. 3, 2014, pp. 15-166.

Raji, Mohammad, et al., "Photo-Guided Exploration of Volume Data Features", arxiv.org, Cornell University Library, Oct. 18, 2017, Ithaca, NY, 14853.

\* cited by examiner

CONSISTENT 3D RENDERING IN MEDICAL IMAGING

RELATED APPLICATIONS

The present patent document is a divisional of U.S. patent application Ser. No. 15/827,263, filed Jan. 3, 2018, which claims the benefit of the filing date under 35 U.S.C. § 119(e) of Provisional U.S. Patent Application Ser. No. 62/469,703, filed Mar. 10, 2017, which is hereby incorporated by reference.

BACKGROUND

The present embodiments relate to medical imaging of three-dimensional (3D) scans. Data representing a volume is rendered for visualization. Due to the many different scan settings and patient variability, renderings for different patients or at different times appear different.

To reduce variability, most existing medical rendering provides a set of static visualization presets for specific workflows or diagnostic contexts. Even with static presets, the rendering may require manual adjustment and may not provide consistent rendered results. Patient and scanner variability may also continue to contribute to inconsistency. Semi-automatic machine learning approaches have been used to provide transfer function design in traditional volume rendering (e.g., ray casting or alpha blending), but may still not sufficiently reduce variability.

Variability is particularly troublesome for physically-based volume rendering, which relies on the physical simulation of light propagation (e.g., unbiased path tracing). Physically-based visualization techniques produce global illumination effects in computer-generated graphics that mimic the real-world interaction of light with various 3D objects or tissues. This results in physically plausible images that are often easier for the human brain to interpret when compared to the more analytical images from traditional rendering. These physically-based visualization techniques are more sensitive to changes in the classification or the interpretation of the underlying medical data. As a result, small changes to the rendering parameters may have a more pronounced impact on the perception and interpretation of 3D structures in the final image as compared to the traditional volume rendering techniques. Obtaining very high quality reproducible images with diagnostic significance is then partially at the user's discretion. While existing techniques for providing visualization presets may help, the resulting rendered images may not have consistent quantitative properties (color, hue, reflectance, etc.) across datasets. Physically-based rendering also takes longer to generate a rendered image, so alteration to reduce variability is time consuming.

SUMMARY

By way of introduction, the preferred embodiments described below include methods, systems, instructions, and computer readable media for three-dimensional rendering. A machine-learnt model is trained to generate representation vectors for rendered images formed with different rendering parameter settings. The distances between representation vectors of the images to a reference are used to select the rendered image and corresponding rendering parameters that provides a consistency with the reference. In an additional or different embodiment, optimized pseudo-random sequences are used for physically-based rendering. The random number generator seed is selected to improve the convergence speed of the renderer and to provide higher quality images, such as providing images more rapidly for training compared to using non-optimized seed selection.

In a first aspect, a method is provided for three-dimensional rendering in a rendering system. A medical imaging system acquires a medical dataset representing a three-dimensional region of a patient. A renderer renders, using different combinations of rendering settings, a plurality of images from the medical dataset. An image processor applies different pairs of the images of the plurality and a reference image to a machine-learnt model. The machine-learned model is trained to generate representation vectors of the images and the reference image. The image processor selects one of the plurality of images based on the representation vectors. The selected one of the plurality of images is displayed.

In a second aspect, a system is provided for three-dimensional rendering in medical imaging. A medical scanner is configured to scan a volume of a patient. A graphics processing unit is configured to three-dimensionally render images from the scan of the volume. The images are rendered with different values for rendering parameters. An image processor is configured to search for one of the images matching a reference image based on a machine-learnt neural network. A display is configured to display the one image of the volume of the patient.

In a third aspect, a method is provided for three-dimensional rendering in a rendering system. A reference image is three-dimensionally rendered with path tracing using a first number of samples per pixel and a first random number generator seed. Other images are three-dimensionally rendered with the path tracing using a second number or less of samples per pixel and other random number generator seeds. The second number is less than the first by a factor of ten or more. An error between the other images and the reference image is measured. One of the other random number generator seeds with a lessor error than the others of the random number generator seeds is identified. The rendering system is configured for path tracing with the identified one of the random number generator seeds.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Two general approaches are described herein. In one approach, a machine-learnt representation network provides for consistent three-dimensionally rendered medical images. This machine-learnt representation approach is described below with respect to FIGS. 1-3. In another approach, pseudo-random sequences for physically-based rendering are optimized. This pseudo-random sequence approach is described below with respect to FIGS. 4-7. These different approaches may be used separately. In other embodiments, these different approaches are combined, such as using the increased rendering speed provided by optimization of the pseudo-random sequence to generate many samples for training for the representation network.

For machine-learnt comparison, an unsupervised neural network maps an image x to a vector representation, denoted f(x). The vector representation has a property. The Euclidean distance between representations of two images is correlated to the difference of their visual effects (i.e., representations of images with similar visual effect will have small Euclidean distance). This representation is used to automatically select rendering parameters of the photorealistic (i.e., physically-based) or other renderer to produce desired visual effects.

Consistent visual interpretation for 3D images may potentially simplify diagnostic workflow and may promote the clinical use of 3D data for decision support. Consistent photorealistic rendered images may be provided in new platforms and workflows, such as fully automated reporting and cloud-based rendering services. Consistency may be provided based on an expert or practice selected reference. A general, adaptable approach using a machine-learnt comparison to a reference is scalable, allowing variance in any rendering parameter. The same approach may be used in a wide variety of clinical problems or circumstances.

Figure 1:
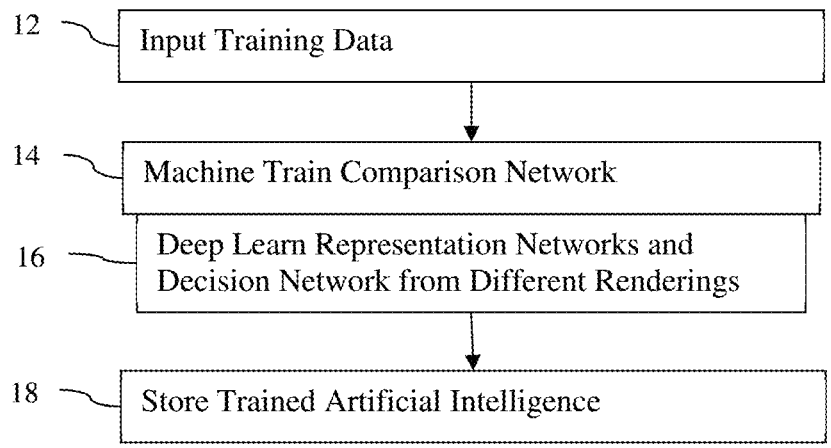
FIG. 1 is a flow chart diagram of one embodiment of a method for machine training for a comparison network.

FIG. 1 shows one embodiment of a method for machine training for comparison. Optimal rendering parameters may be obtained by representation learning to compare different rendered images with a reference image. The input of the artificial intelligence system includes multiple images to compare to a reference, so the training learns to indicate which of the multiple images is most like the reference. Using many examples, the machine learns to provide a scalar indicating the more similar of the multiple images to the reference. This training creates a representation network that provide vectors that may be compared to identify perceptual similarity. The trained network maps the input image to a vector with the property that the Euclidean distance of two vectors correlates with the visual effect difference between the two images. The most similar rendering to the reference is obtained by searching the rendering that leads to the minimum Euclidean distance. The resulting image of the multiple images more likely includes diagnostically useful information or other characteristic reflected in the reference, so is used for diagnosis.

The method of FIG. 1 is implemented by a machine training system, such as by an image processor and a graphics processing unit in a server, computer, or other machine. In one embodiment, the system of FIG. 8 implements the method of FIG. 1, with or without the medical scanner and/or display. For example, data is input by loading from a memory, the graphics processing unit (GPU) renders images to be compared, the image processor performs the training based on the data, and the memory stores the learnt artificial intelligence. As another example, the medical scanner and/or memory input the data to a server, which performs the training and outputs to a memory.

The acts are performed in the order shown (top to bottom) or another order. For some forms of learning, results may be fed back as input in a repetition of the acts.

Additional, different, or fewer acts may be provided. For example, act 18 is not provided, such as where the trained artificial intelligence is used rather than stored for later use.

In act 12, training data is input. The training data is gathered from one or more memories, sensors, and/or scanners. The gathered data may be stored and/or transmitted to a buffer, memory, cache, processor, or other device for training. This gathered training data is input to the machine learning algorithm.

Many samples of the same type of data are input. To learn statistical or other relationships that may be sufficiently complex that a human cannot perceive the relationships in a same level, tens, hundreds, or thousands of samples are provided.

Any data may be used. For representation learning, a pool of three-dimensional volumes is collected. The volumes are scan volumes of one or more patients. The volumes are for a given application, such as vascular computed tomography (CT). Alternatively, the volumes are generic to the application, such as being whole body volumes or volumes representing different parts.

Since the artificial intelligence is to be trained to provide relative similarity or comparison with a reference, three-dimensionally rendered images are used as the training data. For each sample, an image rendered from the scan data representing a patient is used. Any rendering may be used, such as ray casting, surface rendering, projection, maximum intensity projection, or physically-based rendering (i.e., path tracing). Physically-based rendering simulates light propagation through the volume. This is different than illumination or shading used in ray casting or surface rendering, instead using pseudo-random simulation of different paths that may be followed by light. Any path tracing, such as unbiased path tracing, Monte Carlo rendering, global illumination, or other simulations of light propagation may be used.

Since the representation learning is to compare two different images to a reference image, the samples used for training are grouped in sets of three. Where representations for additional images are included in the network architecture, samples in other size groupings (e.g., four images) may be provided.

In one embodiment, six images are rendered for each volume, V. Three images are rendered using the same camera position $\phi_0$, and with random rendering parameters $\phi_i$, i=1,2,3. The images are denoted as $R(V, \phi_0, \theta_i)$, i=1,2,3. Then, three camera positions $\phi_i$, i=1,2,3 are randomly generated, and three images $R(V, \phi_i, \theta_i)$, i=1,2,3 are rendered for the three camera positions. The rendering parameters used for the images from the three different camera positions are the same rendering parameters used for the images from the same camera position. The six images generated in this way are referred to as a "dataset." The process is repeated to generate N datasets for each 3D volume, V. Other numbers of images, sets of random rendering parameters, numbers of camera positions, and/or numbers N (e.g., tens, hundreds, or thousands) may be used. The same volume may be used to create more than one dataset or set of six images.

Any rendering parameter may be varied. Camera position is treated separately, but may be a rendering parameter. Other rendering parameters include the transfer function, window, bounding box, scaling, level compression, data normalization, type of virtual lights, position of the virtual light sources, orientation of the virtual light sources, image-based lighting sources, and/or clip plane position. For physically-based rendering of photorealistic images, additional rendering parameters include material properties, such as reflectance, a global albedo, transparency, and/or surface roughness. Other renderer-specific parameters may be used, such as the seed for random number generation in Monte Carlo path tracing.

The values for one or more rendering parameters are randomly selected. Non-random or patterned selection of the values may be used. Some, one, or all but one rendering parameters may be assigned a constant value, such as changing the transfer function while maintaining the clip plane in a user set position for each of the renderings. A range of values or group of values may be used for random or patterned selection to generate the images with different settings of the rendering parameters. As discussed below for selection, the value or values may be determined based on an optimization.

Figure 4:
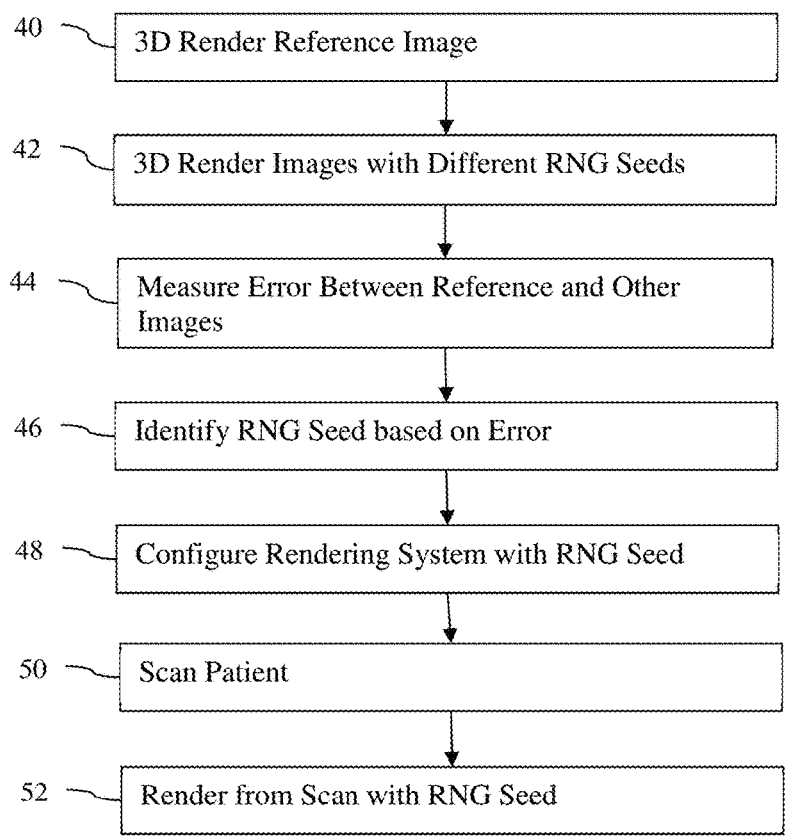
FIG. 4 is a flow chart diagram of an embodiment of a method for improving physically-based rendering speed by seed selection.

To generate the samples, many renderings are performed. Since the renderings are for training, any amount of time may be used to render. Physically-based rendering is more processor and time consuming than ray casting. To allow a greater number of renderings and corresponding samples for training and/or reduce the time needed for physically-based rendering, a random number seed optimized to allow rendering with fewer light-path samples is used. For example, a seed optimized as discussed below for FIG. 4 is used.

For training, the goal or ground truth information is input. The artificial intelligence system is trained with labeled data (e.g., input triplets of images and corresponding desired output). For training for comparison, triplets of images are input. The ground truth is which of two of the images is more similar to the third. This binary ground truth is a 0 or negative for one image and a 1 or positive for the other image. In other embodiments, a non-binary scalar is used, such as a relative amount of similarity to the reference.

The images from the different camera angles for each triplet sample are assigned the same ground truth. The triplet with different angles is assigned the same ground truth as the triplet with the same angle. To train the network, triplets of images from different camera positions and their ground truth relationship are acquired.

The ground truth is calculated from the triplets. Denoting the three images as R (reference), A, B, the ground truth relationship tells if A or B is more similar to R. The ground truth relation is obtained in the following steps. Given the triplet of images from the same camera position, denoted as R', A' and B', the perceptual hash values between the R' and A', and R' and B' are computed. A smaller perceptual hash value indicates a similar visual effect and indicates if A' or B' is more similar to R'. The perceptual hash may be calculated on a pair of images that are aligned (e.g., images from the same camera position) and may not be directly applied on the triplet with difference camera positions. Since R, A, B have the same rendering parameters as R', A', B', and the same rendering parameters indicate same visual effect, the ground truth relationship calculated for R', A', B' is directly transferred to R, A, B.

The perceptual hash metric is denoted as PH(•,•). For each dataset, a level of perceptual similarity between each of two images (2 and 3) to a reference image (1) of the triplet from a same camera angle. These two perceptual hashs are calculated as: $D_{12}=PH(R(V, \phi_0, \theta_1), R(V, \phi_0, \theta_2))$ and $D_{13}=PH(R(V, \phi_0, \theta_1), R(V, \phi_0, \theta_3))$. While the perceptual hash value may be used as the ground truth, the perceptual hash values are used to generate the binary ground truth in other embodiments. The binary around truth or scalar value, y, is calculated as:

$$y = \begin{cases} 1, \text{ if } D_{12} < D_{13} \\ 0, \text{ otherwise} \end{cases}.$$

If y is 1, then image 3 is more similar to the reference image 1 than image 2. If y is 0, then image 2 is more similar to the reference image 1 than image 3. Other metrics than perceptual hash may be used, such as other perceptual metrics, minimum sum of absolute differences or other correlation.

Based on the provided datasets and calculated ground truth, the artificial intelligence system is trained to produce the desired output from any input. In act 14, the artificial intelligence or intelligence is machine trained. The collected samples (e.g., the triplets from different camera angles), including ground truth (e.g., binary relative perceptual similarity calculated with perceptual hash), are used to train a comparison network. A machine, such as an image processor, computer, server, or other device, learns from the samples to indicate which of two input images are more similar to a reference image. Using machine-learning, complex statistical relationships between large numbers (e.g., tens, hundreds, thousands, or more) of input variables to any number of output variables are extracted from the large number of samples.

The training is for imaging in any context. One model may be learned for any number of imaging situations. Alternatively, different models are trained for different situations. The different situations may include different scan modalities (e.g., different model for computed tomography, magnetic resonance, ultrasound, positron emission tomography, and single photon emission computed tomography). The different situations may include different types of tissue of interest (e.g., liver versus kidney), different diagnostic purpose or workflow (e.g., cancerous lesion versus bone calcification), and/or different users (e.g., different operators may have different preferences for visualization).

Any now known or later developed machine learning may be used. Regression, classification, and/or reinforcement learning are used. Regression training learns a range or continuous output by minimization of a metric. Classification learns disparate outputs. Reinforcement learning learns a sequence of actions with feedback. Neural network, Bayes network, or support vector machine training may be used. Hierarchal or other approaches may be used. Supervised or semi-supervised machine learning may be used.

To train, features are extracted from the input data. Haar wavelet, steerable, or other features may be extracted from the scan dataset or images. Alternatively, the input data itself (e.g., pixel or color values of the rendered image) is used and the learning determines features, such as with deep learning.

Act 16 represents an embodiment of act 14. The comparison network is trained with deep learning. The deep learning provides representative learning. The training learns convolution kernels from the input images to generate a representation that may be used for a comparison decision. Deep learning (e.g., deep structured learning, hierarchical learning, or deep machine learning) models high-level abstractions in data by using multiple processing layers with structures composed of multiple non-linear transformations, where the input data features are not engineered explicitly. A deep neural network processes the input via multiple layers of feature extraction to produce features used to derive comparison results. The deep learning provides the features used by other machine training to learn to output the comparison. Other deep learnt, sparse auto-encoding models may be trained and applied. The machine training is unsupervised in learning the features to use and how to classify given an input sample (i.e., feature vector).

Using deep learning, the input features required for the machine learning are not engineered by the user explicitly, as in shallow learning algorithms. This is especially useful with render settings, which may not have an explicit natural relationship with the input data. Deep learning figures out the data features that end up providing a good classifier or model for the comparison network. Deep learning is effective in extracting high level abstractions (features) from low level input data (e.g., raw images) that is suitable for the trained task, so may be more convenient than and superior to hand-crafted features for identifying features for render settings.

Any neural network architecture for the deep learning may be used. The neural network architecture defines the neural network used to train and the resulting trained or machine-learnt comparison model. For example, a set of layers (e.g., representation network) is used to generate features at any level of abstraction from the input images, and another layer or group of layers is used to make a comparison based on the values of the features.

Figure 3:
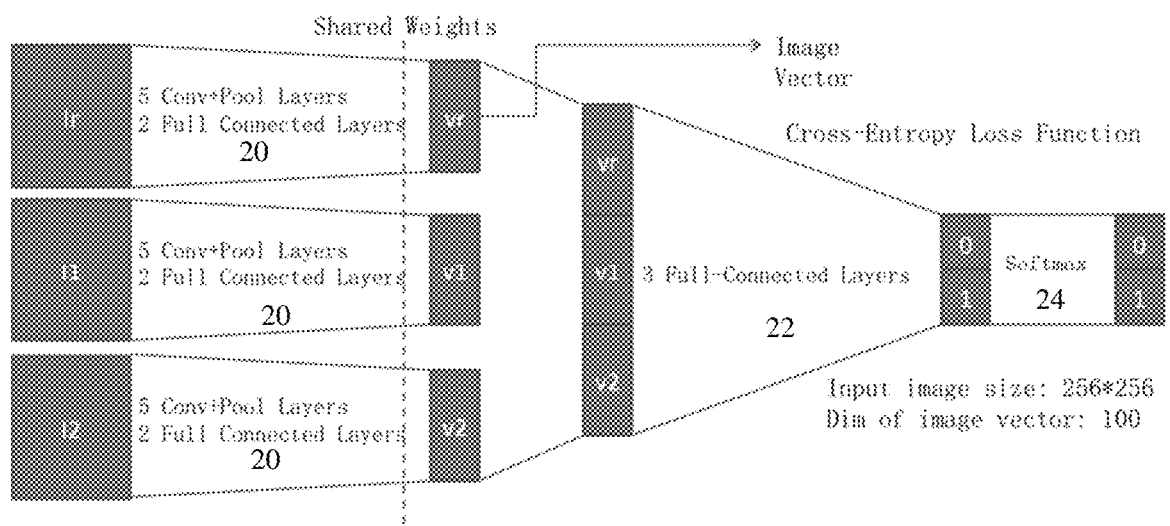
FIG. 3 illustrates a neural network architecture for a comparison network.

FIG. 3 shows one example architecture used for the comparison network. A convolutional neural network (a.k.a., representation network) 20 is created. The same convolutional neural network is used for each input image of the triplet. The representation network 20 is shown in FIG. 3 three times, once for each of a triplet of images (i.e., reference image $I_r$, comparison image 1, $I_1$, or comparison image 2, $I_2$). The representation network 20 is trained to output a vector of a fixed length. In the example of FIG. 3, the vector includes 100 values for images that are 256×256 pixels. The convolutional neural network is denoted as f(v), and its output vector, v, is referred to as the "representation" of the image (i.e., an image vector). In the example of FIG. 3, the representation network 20 has five convolutional and pooling layers and two fully connected layers, but other layer arrangements may be used.

The architecture includes a network for comparing based on the vectors from the representation network. A neural network (a.k.a., decision network) 22 receives as input the three "representations", denoted as $f(v_1)$, $f(v_2)$, $f(v_3)$, and learns to output a scalar between 0 and 1. The scalar represents the possibility that the visual effects of $v_1$ and $v_2$ are closer than that of $v_1$ and $v_3$. In the example of FIG. 3, the neural network 22 for the decision network is formed of three fully connected layers, but other layer arrangements may be used. The decision network 22 is used for training the representation networks.

Softmax represents the function where the scalar values for the two comparison images sums to 1. For example, the decision network learns to output two values that sum to 1, such as outputting 0.25 and 0.75 for one triplet and 0.4 and 0.6 for another triplet. In another embodiment, one scalar value is output for a comparison with the difference from 1 being assigned as the scalar value for the other comparison. Other output functions may be used, such as a binary indication for each comparison image or other values that may not sum to 1.

The entire neural network is formed by the arrangement of the three separate representation networks without outputs connected to the decision network. This neural network architecture takes three images as input, and outputs a scalar value. The neural network is trained using $R(V, \phi_i, \theta_i)$, i=1,2,3 as input, and y as output. Other architectures may be used, such as replacing the decision network with triplet loss options designed to train the network with triplets.

Any deep learning may be used. The representation and decision networks are trained together, but may be separately trained. In one embodiment shown in FIG. 3, a cross-entropy loss function is used to train. Other functions measuring the difference of a current output from the ground truth and optimizing the neural network to minimize the difference may be used.

The machine trains to output a comparison that may be used to find a rendered image most similar or sufficiently similar (e.g., within a threshold amount based on the scalar value) to a reference image. The machine-learnt comparison model may be used to provide consistent imaging. The path tracing, other physically-based rendering, or other rendering with settings resulting in a similar or consistent image is identified using the trained comparison model.

In act 18, the trained artificial intelligence is stored. The result of the training is series of tensors. Each tensor represents the weights of one layer of the neural network. The tensors represent the learned knowledge through machine training. In one embodiment, the representation network is stored. The decision network is used to train, but not for application so is not stored.

The trained representation model is stored in a memory. Any memory may be used. The memory used for the training data may be used. For application, the memory may be in another device. For example, the trained model is stored in a memory of a medical imager or workstation. The medical imager or workstation uses the trained model to select an image and/or corresponding rendering parameter settings. A server implementing one copy of the trained comparison model may be used to identify for different patients. Multiple copies of the trained model may be provided to different physicians, medical scanners, and/or workstations for use by different physicians for different patients.

Figure 2:
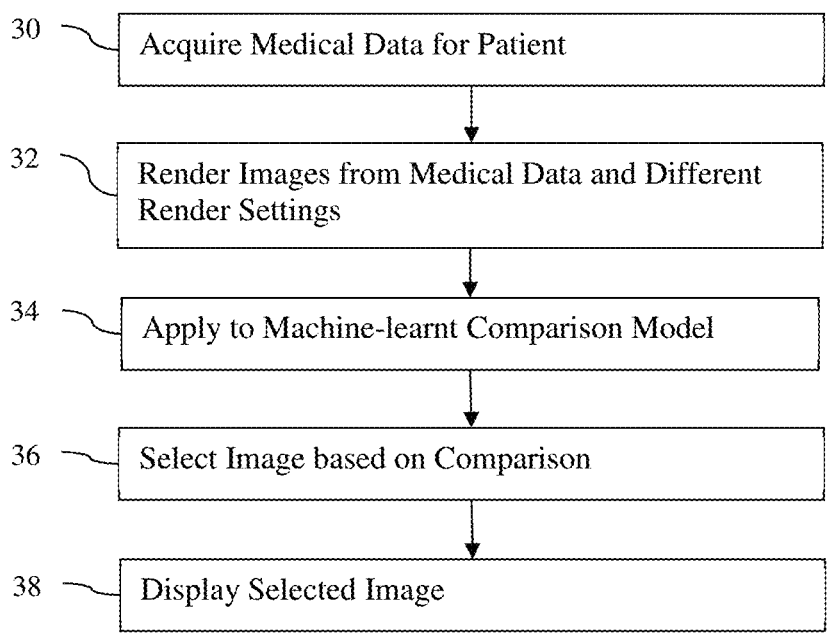
FIG. 2 is a flow chart diagram of an embodiment of a method for rendering a reference consistent image.

FIG. 2 shows one embodiment of a method for three-dimensional rendering in a rendering system. The method applies a machine-trained representation model or neural network to identify an image or rendering settings for producing an image consistent with a reference.

Figure 8:
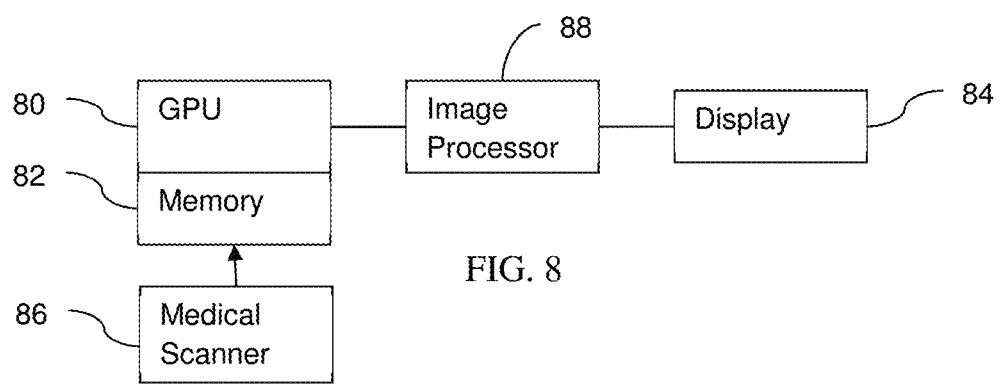
FIG. 8 is a block diagram of one embodiment of a system for three-dimensional rendering.

The rendering system is the system of FIG. 8 or a different system. For example, the rendering system includes a renderer (e.g., GPU) for rendering images and an image processor for selecting an image using the machine-learnt comparison model.

The acts are performed in the order shown (top to bottom or numerical) or other orders. Additional, different, or fewer acts may be provided. For example, acts for optimizing the seed selection for the random number generator in path tracing rendering are provided. As another example, the selected image is stored or transferred over a network instead of or in addition to display in act 38. In another example, acts 32 and 34 are repeated any number of times before or as part of performing act 36.

In act 30, a medical scanner acquires medical data. The medical scanner provides medical data representing a 3D region of the patient. The medical scanner may directly provide the medical data, such as providing in an image processing pipeline of the medical scanner. The medical scanner may indirectly provide the medical data, such as routing the medical data through a memory or computer network. The medical data may be accessed from a picture archiving and communications server.

The medical data is for a given patient. While the training may use samples from many patients, the learnt model is applied to the medical data for a patient to identify an image or corresponding rendering settings for consistent imaging of that patient. The same or different machine-learnt models are applied to data for any number of patients.

Any type of medical data is obtained. Scan data representing a volume is loaded. The scan data may be from multiple two-dimensional scans or may be formatted from a three-dimensional scan. The medical data represents a three-dimensional region of the patient, such as being a set of voxel values for voxels distributed along three spatial dimensions.

Any imaging modality and corresponding medical imaging system may be used. Example medical scanners include magnetic resonance, computed tomography, ultrasound, positron emission tomography, and/or single photon emission computed tomography.

In act 32, a renderer renders a plurality of images from the medical dataset. The volume of the patient is rendered in different ways. Different combinations of rendering settings are used. One or more rendering settings may be constant for rendering the images, but at least one rendering parameter is varied. The training may vary the same or greater number of rendering parameters. Alternatively, all the rendering parameters may be varied.

The settings may be randomly assigned or assigned using a pattern, such as rendering images with a representative sampling of the possible settings. The user may control or select the settings for parameters and/or parameters to be varied. Any number of images may be rendered, such as five or more, tens, or hundreds. For each combination of rendering settings, an image is rendered.

Figure 6A:
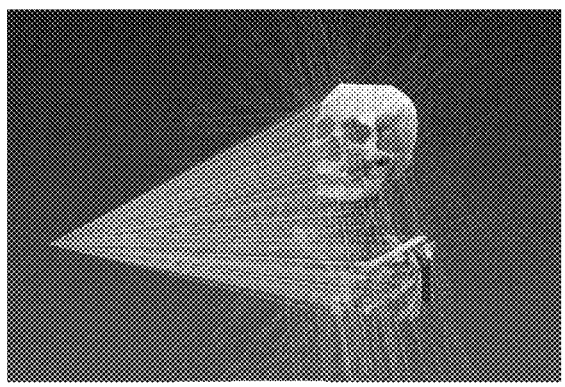
FIGS. 6A and 6B show different path samplings due to differences in seed.
Figure 6B:
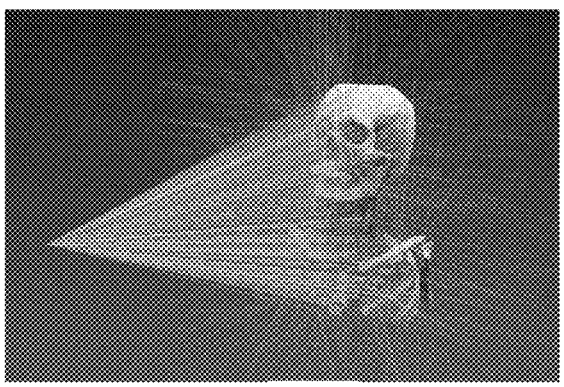

Any type of rendering may be used, such as the same or different type of rendering used for training. For example, ray casting is used. As another example, a physically-based renderer renders photorealistic images of the volume region of the patient using different sets of values for the rendering parameters. The physically-based renderer is a graphics processing unit, array of graphics processing units, workstation, server, computer, or other machine capable of the required computations. Any physically-based rendering algorithm capable of computing the light transport may be used, such as path tracing, unbiased path tracing, Monte-Carlo path tracing, or Metropolis light transport. The physically-based rendering simulates the physics of light propagation (e.g., emulates photon interaction) to create an image instead of accumulating volume samples with local illumination along viewing rays from the camera, as is done for traditional volume rendering. In path tracing implemented for physically-based rendering, the paths of light or photons, including due to scattering and/or absorption, are modeled and used for rendering. FIGS. 6A and 6B show example light paths, including many paths having at least one instance of scattering as represented by a change in direction. The physically-based rendering result may be built up over time as the rendering may rely on probabilistic scattering and tracing many light paths. For each pixel of the image being rendered, any number of light path samples are used. For example, 16-2000 samples are used for each pixel.

In one embodiment, the renderer renders with Monte Carlo path tracing. The random number generator of the Monte Carlo path tracing generates a sequence of pseudo random numbers used to determine scattering or the paths of light. One seed may result in fewer samples needed before a rendered image provides sufficient information. Using the method of FIG. 4, various seeds may have been tested in an optimization. The seed used for rendering for a given patient is selected as part of a previous optimization so that the images may be rendered more rapidly given a same rendering capability than if a different seed were used. Non-optimized seeds may be used for rendering. The seed optimization may be performed as part of rendering for a given patient, such as using different seeds for different renderings and testing as described for FIG. 4.

The rendering results in a photorealistic image. For a given rendering or settings of rendering parameters, a sequence of images may be provided as the image is built or rendered. Alternatively, for a given set of values of rendering parameters, a single image is output. Multiple, such as ten, twenty, or more images are rendered using different settings. A sequence or group of images due to alteration of values for one or more rendering parameters may be output.

In act 34, an image processor applies the rendered images for the volume and a reference image (i.e., applies a triplet) to the representation network part of machine-learnt model. Any reference image may be used. For example, an expert selects or creates a reference image. As another example, a hospital, medical association, physician, or other person determines an ideal or desired image for a given application (e.g., CT vascular). A previously created image for a given physician may be used. An image from a clinical study, literature, or medical atlas may be used. In one embodiment, a panel or plurality of possible reference images are displayed, and a user selects the reference image from the panel. In another embodiment, a previous image of the patient, such as from a previous scan or examination, is used.

The rendered images are applied in sequence. As each image of the new or current volume is rendered, the new image is compared with the reference image.

For applying the images in the representation part of the machine-learnt model, the images are processed by the image processor, such as a computer, medical scanner, workstation, or server. The image processor uses the internal representation of the representation network of the machine-learnt model. Given a reference image provided by the user, denoted as R, the representation network is applied on the image to get a vector, denoted as $f(R)$. For any given rendering parameter, $\theta$, the rendered image is denoted as $X(\theta)$. The rendered image is applied to the representation network to get a vector $f(X(\theta))$. The image processor inputs the images, resulting in the machine-learnt model outputting the vectors from the representation network for the two images.

Where the reference image is previously determined, the representation $V_r$ may be previously determined. Alternatively, the reference image is applied at a same time as the rendered images for the patient.

The machine-learnt model was previously learned as discussed above. The machine-learnt model was trained to indicate ones of the pairs of images that is more similar to the reference image. The decision network part of the machine-learnt model is not used for application. Instead, the representation network is used as the machine-learnt model to provide vectors representing the reference image and images rendered differently. Random or other variation in rendering settings and/or camera positions are used to train the machine-learnt model to compare with common or possible variation in rendering. The trained model is used to find representations that reflect similarity in perception. In one embodiment, the machine-learnt model is a neural network with an architecture shown as the representation network 20 in FIG. 3. The convolutional neural network taught to output a feature vector for each of the images is used. The machine-learnt model was trained with any metric of similarity, such as a perceptual hash metric, based on the representation networks 20 and the decision network 22.

For consistency, the application of the machine-learnt model is more likely to provide a vector for rendered images (e.g., photorealistic image) of the patient volume that may be used to compare to a vector for a standard or reference image despite differences in the volume, medical scanner, medical scanner configuration, or other differences. The machine-learnt model is trained to output representation vectors of fixed length, which may be used for comparison. The machine-learnt model (i.e., representation network) is used to provide consistency over time for a patient, in a practice, for an application, and/or across patients.

In act 36, the image processor selects one of the rendered images based on the representation vectors from application of the machine-learnt model. The most similar one of the rendered images of the patient volume to the reference image is found through repetition of acts 32 and 34. A sufficiency threshold may be used, such as searching for an image that has a similarity above a threshold. The repetition continues until a rendered image that is perceptually similar to the reference image is found. By comparing representation vectors from multiple images to the representation vector of the reference image, an image more similar than any of the other images may be identified.

To select, the distance between representation vectors is calculated. For example, the Euclidean distance between the two vectors, $D(\theta)=\|f(X(\theta))-f(R)\|_2$ is determined. Other distances between representation vectors may be used. The distance is a function of $\theta$. The rendered image with the minimum distance is selected.

In one embodiment, the rendering of act 32 and the selection of act 36 are performed with a search strategy. The rendering of act 32 and application of act 34 are performed with different combinations of the rendering settings selected as part of an optimization. The graphics processing unit renders new images to mimic the effect of the picked reference by searching for the rendering parameters that minimize the Euclidean distance between the representation of the rendered image and the representation of the picked reference. To find the setting of the rendering parameter that provides the most similar visual effect to R, an optimization problem is solved. $\theta$ that minimizes $D(\theta)$ is found. Such optimization problem may be solved using standard optimization techniques, such as hill climbing or gradient descent. Which rendering parameters to change and/or how much to change the setting is based on optimizing. Based on the distances between vectors of different images from the reference image, different magnitudes of change and/or selections of rendering parameters to change are tested by rendering and performing further comparison. The results are used to inform the magnitude and/or selection of rendering parameter for the next rendering.

In act 38, the selected rendered image is displayed. Other images of the plurality of rendered images, the reference image, or other images may be displayed. The rendering parameter settings for the selected image may be used for rendering subsequent images, such as from different camera positions or other rendering interactions from the user.

The rendered image of the patient is displayed. This displayed image is more consistent in appearance with the reference image due to the application of the machine-learnt comparison model. By displaying the selected image, a rendered image more consistent with the reference is provided. As a result, the image may more likely include diagnostically recognizable information, may be more easily analyzed, and/or may be used for comparison with expected or past results. The time spent reviewing may be reduced due to consistency. The ability or likelihood to recognize diagnostically useful information may be increased.

The renderer, host computer of the renderer, or other device transmits the photorealistic image or images to a display device. The transmission is over a bus, through a network interface, over a network, from a memory, or from a display plane. For example, the image is loaded into a buffer and output from the buffer to a display for viewing by a physician to aid diagnosis or pre-operative planning. A computer-generated representation of the volume of the patient suitable for viewing by human users (e.g., 2D images, videos, stereoscopic image pairs, volumes, holograms, or lightfields) is output. Alternatively, the output may be for storage and/or for further machine analysis.

In another embodiment, the display of the image is an initial image for interactive viewing. The machine-learnt model is used to initialize interactive viewing applications in the clinical workflow. By providing values for rendering parameters so that the images are consistent with an established visualization design, the amount of user interaction may be reduced.

FIG. 4 is a flow chart diagram of one embodiment of a method for three-dimensional rendering in a rendering system. Due to the time needed to render (e.g., seconds or minutes) using physically-based rendering (e.g., global illumination volume rendering using Monte Carlo sampling), interactive performance of the rendering is limited. While this computationally expensive rendering may produce high quality images with improved perception of depth cues, the rendering uses a high number of samples per pixel to compute the rendering equation. The method of FIG. 4 uses a self-optimizing random number sequence for the path tracing, allowing better approximation of the final image with a smaller number of samples. Path tracing randomly samples light paths between the virtual camera and the light sources, through the volumetric data or surfaces. The computation uses a sequence of random numbers to compute light scattering for a single light path. An optimized sequence may allow the initial images produced by the renderer, using only a small number of light path computations, to better approximate the final result of the light transport simulation using a greater number of light path computations. To compute the light paths in an optimized order, the sequence of light scattering direction is controlled indirectly by manipulating the seed used for the pseudo-random number generator.

The method is performed by the system of FIG. 8 or a different system. For example, a renderer performs acts 40, 42, and 52, an image processor or controller performs acts 44-48, and a medical scanner performs act 50. Other devices may perform or be used in performance of any of the acts.

The acts are performed in the order shown or other orders. For example, acts 40 and 42 are performed in any order. Additional, different, or fewer acts may be performed. For example, acts 50 and/or 52 are not performed.

Figures 5A, 5B, 5C, 5D:
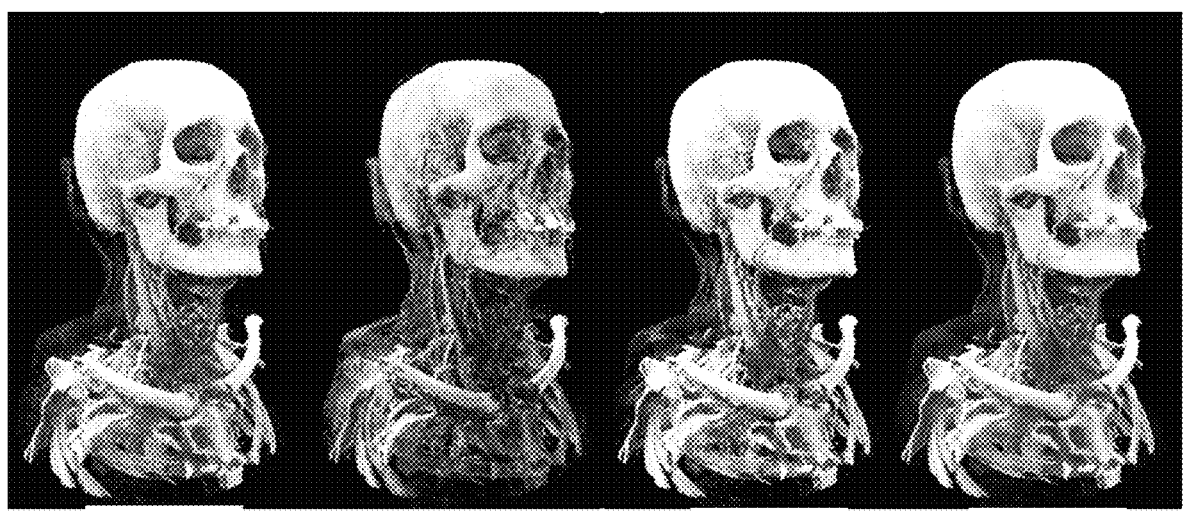
FIGS. 5A-D show different example physically-based renderings.

In act 40, a renderer three-dimensionally renders a reference image. The reference image is rendered with path tracing using a first number of samples per pixel and a first random number generator seed. Any seed may be used, such as a default seed, a seed based on internal operation of a processor (e.g., time), or other seed. Any number of samples per pixel (i.e., number of light-paths traced in the volume per pixel) may be used, such as hundreds or thousands. The rendering provides a reference or desired image. For example, FIG. 5D shows a physically-based rendering using 2000 samples per pixel for a given seed.

In one embodiment, a user selects and loads a representative volume (e.g., scan data) and rendering configuration that produces images with a variety of light paths. The volume used for the seed optimization may be an example of real data for which the best rendering is to be provided (e.g., vascular CT volume) or a special volume used to find a seed that produces improved results over a variety of data. The types, sizes, and/or numbers of surfaces, textures, boundaries and/or other characteristics represented in the volume may be considered in selecting the volume to create the reference image. For example, the selected volume contains structure for a variety of light interactions (e.g., interactions with convex surfaces, concave surfaces, semi-transparent regions, clip planes, areas in light and shadow, etc.).

The reference image is rendered to be application specific (e.g., for a particular organ, disease, or test) or may be generic to two or more applications. A full resolution reference image is generated with a large number of samples per pixel.

In act 42, the renderer three-dimensionally renders other images with the path tracing using a lower number of samples per pixel and other random number generator seeds. Any different candidate seeds may be used, such as random or pseudo-random selection of seeds. The seeds may be from a list, such as sequencing through the list. Any selection of the different seeds may be used, such as using time as each rendering is performed. Since the relationship between the values of the seed and the resulting image rendered using the seed is not direct, any selection may be used.

Any number of different seeds and corresponding different rendered images may be used, such as five or more, tens, hundreds, or thousands. The identification of an acceptable seed may be performed as a pre-process or before use of the seed for a given patient, so there may be any amount of time and/or processing power available. The settings or values of other rendering parameters are kept constant for the different renderings, but may also vary.

The number of samples per pixel is limited, such as being less than the number of samples per pixel used in the reference by a factor of two, four, ten, or more. For example, the reference uses 2000 samples per pixel and the renderings with other seeds use 200 or less (e.g., 20 or less). The rendered images of FIGS. 5A-C use 16 samples per pixel compared to the 2000 samples per pixel of FIG. 5D. A small number of samples is used since a small number results in more rapid rendering time, allowing for more responsive interactive rendering. An image with sufficient information to allow a user to decide whether to change the rendering (e.g., camera position, transfer function, window, or material property) is rendered more quickly using fewer samples per pixel.

The rendering of acts 40 and 42 uses or emulates coherent scattering in the path tracing. Coherent scattering improves the memory caching efficiency, leading to significant performance improvement at runtime (e.g., 30% to 100+% improvement in rendering speed, depending on data classification, GPU architecture and other factors). Coherent scattering also lowers the perceived spatial variance in the image at the cost of slower convergence speed and temporal artifacts during image refinement. Coherent scattering may be used during interactive rendering with a small number of samples per pixel, where sub-optimal light paths may lead to larger image differences compared to the non-coherent scattering.

In act 44 of FIG. 4, an image processor measures an error between each of the rendered images and the reference image. Any metric may be used, such as a measure of similarity or correlation. In one embodiment, a perceptual metric is used, such as a perceptual hash. The error between the reference image and an image rendering with a given, fewer number of samples per pixel than the reference image is calculated.

In an alternative to fixing the number of samples, the error measurement of act 44 may be used with the rendering of act 42 to measure the number of samples per pixel when the error reaches a threshold. The rendering continues by adding more samples. For each iteration (e.g., every 10 or 100 additional samples per pixel), the measurement of act 44 is performed again. This continues until the error between the rendered image and the reference image is below a threshold. The RNG seed that produces faster convergence toward the reference image (i.e., fewer number of samples per pixel to reach the threshold error), rather than optimizing the interactive image quality, is found. For each candidate seed, any number of light paths are used in rendering based on the number of samples required to lower the error metric to a given threshold.

In act 46, the image processor identifies one of the RNG seeds. The RNG seed that results in a rendered image with a lesser error than the other seeds is selected. Alternatively, the seed that results in a sufficient error with the lowest number of samples per pixel is selected.

By repeating the rendering of act 42 and the measurement of error of act 44, the seed resulting in a rendering with a fewer number of samples is found. The repetition continues until a seed providing an error below a threshold is found. Alternatively, the repetition continues until a given number, N, of candidates are evaluated, and the seeds with the lowest metric or number of samples per pixel meeting a metric is selected.

In act 48, a rendering system is configured for path tracing with the identified seed. The image processor may configure the renderer. Alternatively, the seed is passed to a different system. A renderer of the different system is configured by loading or using the selected seed. The identification is performed as pre-processing. The identified seed is then passed to any number of other rendering systems for use in rendering volumes for patients.

Different seeds may be identified for different applications. The different seeds are used to configure the rendering system for rendering in respective different applications. Alternatively, a seed is identified generically and used in any application.

The seed identified in act 46 allows the renderer to produce an image close to the reference image with fewer samples per pixel, so more rapidly. The optimized random number generator (RNG) sequence resulting from the selected seed produces improved results for interactive rendering with a low number of samples as compared to the rendering of the reference image.

FIGS. 5A-D illustrate the effect of the optimized RNG seed on the image quality during interactive rendering.

FIGS. 5A-C are rendered with only 16 samples per pixel. In contrast, the result in FIG. 5D is rendered with 2000 samples per pixel. FIG. 5A illustrates a rendering with randomized scattering, resulting in significant spatial noise. FIG. 5B illustrates a rendering with coherent scattering with a non-optimal seed (i.e., using a seed chosen without the FIG. 4 method). In FIG. 5B, the color differs significantly from the reference image since the most important light paths have not been sampled yet. In contrast, FIG. 5C approximates the reference image more closely with reduced spatial noise at 16 samples per pixel by leveraging both coherent scattering and optimized light path evaluation. Coherent scattering is an independent feature, which improves the speed of rendering. The optimized seed allows further improvement using a small number of light-paths. Unlike in non-coherent sampling, light paths for nearby pixels are traced in such a way that they follow similar paths through the volume in coherent scattering. However, this means that entire images worth of light paths may all miss the important directions in the initial samples. By using the optimized seed, the initial samples used in coherent scattering are less likely to miss the important directions. With sufficient sampling, all three configurations reach the reference image. The optimization allows an image with many fewer samples per pixel to be closer to the reference image.

FIGS. 6A and 6B illustrate the initial 16 light paths computed per pixel. FIG. 6A uses the non-optimized seed of FIG. 5B. FIG. 6B uses the optimized seed of FIG. 5C. As shown in FIG. 6B, a more uniform sampling of the light directions without explicit prior knowledge of the data or the lighting environment is provided due to seed selection.

Figure 7:
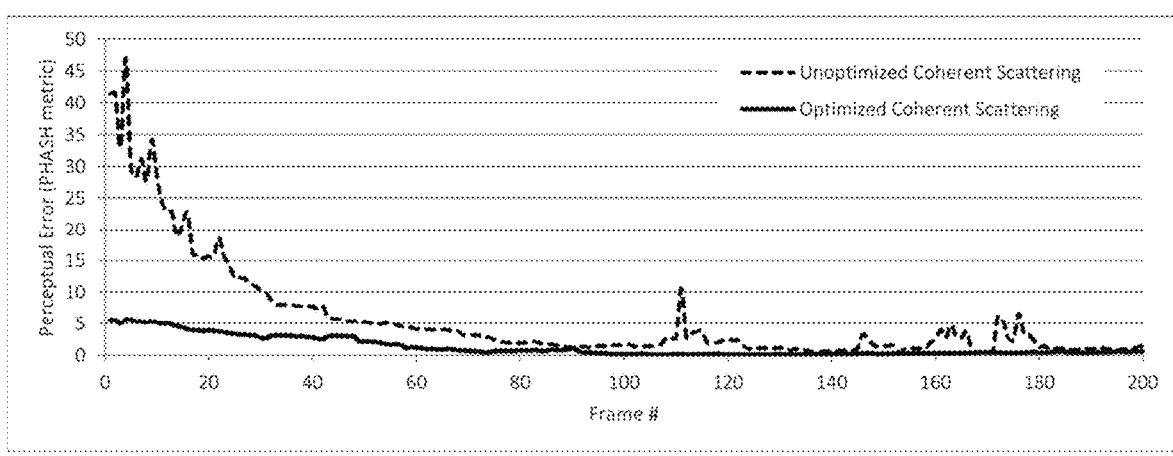
FIG. 7 shows example perceptual errors based on seed.

FIG. 7 illustrates the error progression over the number of samples per pixel. The error (e.g., perceptual hash difference from a reference image) decreases as more samples are integrated into the final image. The dashed line is for the unoptimized seed used for FIG. 5B. The solid line is for the optimized seed used for FIG. 5C. While in both cases, the image is visually indistinguishable from the reference image at above 2000 samples per pixel, the initial refinement which the user sees during interactive rendering is heavily dependent on the RNG stream. The seed selected in act 46 (i.e., optimized seed) provides a physically-based rendered image more similar to the reference image after a much fewer number of samples per pixel. Even after a few samples per pixel (e.g., 5), the image from the optimized seed has a much smaller (e.g., perceptual hash error of 5 against the reference image) than the unoptimized seed (e.g., perceptual hash error of 40 against the reference image).

The more rapid rendering allows the user to interact and change rendering more quickly. Since fewer samples per pixel are needed to have an image closer to the final image, the user may more responsively adjust. Rather than waiting for the completion of the rendering at many samples per pixel, the changes may be made earlier in the progressive rendering used in path tracing. The effect allows coherent scattering to be used during interaction as well, leading to performance improvement and lowered spatial noise.

The optimized seed may be used in any of various situations. In an embodiment shown in FIG. 4, the seed is used for rendering for a given patient. In act 50, the patient is scanned. The previously selected seed is used to configure the rendering system in act 48. The rendering system then three-dimensionally renders from the scan data of the patient in act 52. The image of the patient is rendered with path tracing using a fewer number or lesser number of samples per pixel than the reference image used for optimizing. An initial or progressively rendered image more closing appearing as the reference is provided. The progressive rendering may continue by adding additional samples per pixel or may be ceased to save time and processing power. The earlier, good quality rendered image allows for more responsive interactive rendering.

In another embodiment, acts 42-48 are performed as part of performing acts 50 and 52. The optimization of the seed occurs as part of rendering a sequence of images from a scan of the patient. As the user interacts, different renderings are performed. For example, as the user rotates the camera position relative to the volume, multiple (e.g., four or ten) renderings may be performed. Each rendering uses a different seed. The error is measured from the reference image to identify any seed providing for similar appearance after fewer number of samples per pixel. If or once such as seed is identified, that seed may then be used for rendering other images in the sequence for that patient.

In yet another embodiment, the seed is used to render for training a neural network or other machine learning. Rather than performing renderings using many samples per pixel, time and processing may be saved by using the optimized seed and limiting the number of samples per pixel. Many rendered images may be generated more rapidly due to the seed optimization. The machine training (e.g., deep learning) uses images generated with the identified random number generator seed. The seed may be used in other rendering situations. For example, the renderings of act 32 of FIG. 2 use the optimized seed.

FIG. 8 shows a block diagram of one embodiment of a system for three-dimensional rendering in medical imaging. The system implements the method of FIGS. 1, 2, and/or 4. The system is for training with machine learning (e.g., FIG. 1) and/or application of a machine-learnt model (e.g., FIG. 2). The machine learning is used for comparison of images with a reference image to identify an image and/or rendering settings for consistent rendering. Alternatively or additionally, the system is for identifying and/or applying a seed used for pseudo-random number generation in path tracing (e.g., FIG. 4). Other methods or acts may be implemented, such as providing a user input (e.g., mouse, trackball, touch pad, and/or keyboard) and user interface for interactive rendering.

The system includes a GPU 80, a memory 82, a display 84, a medical scanner 86, and an image processor 88. Additional, different, or fewer components may be provided. For example, the medical scanner 86 and/or memory 82 are not provided. In another example, a network or network connection is provided, such as for networking with a medical imaging network or data archival system. A user interface may be provided for interacting with the GPU 80, image processor 88, or other components.

The GPU 80, memory 82, image processor 88, and/or display 84 are part of the medical scanner 86. Alternatively, the GPU 80, memory 82, image processor 88, and/or display 84 are part of a server, workstation, or computer separate from the medical scanner 86. In other embodiments, the image processor 88, memory 82, and/or GPU 80 are part of a remote server for interacting with the medical scanner 86, which includes the remaining components. The GPU 80, memory 82, image processor 88, and/or display 84 may be a personal computer, such as desktop or laptop, a workstation, a server, or combinations thereof. In yet other embodiments, the GPU 80 and memory 82 are part of a separate computer from the image processor 88.

The medical scanner 86 is a medical diagnostic imaging system. Ultrasound, CT, x-ray, fluoroscopy, positron emission tomography (PET), single photon emission computed tomography (SPECT), and/or MR systems may be used. The medical scanner 86 may include a transmitter and includes a detector for scanning or receiving data representative of the interior of the patient. Scan data is acquired and used for diagnosis or surgical planning, such as identifying a lesion or treatment location.

The medical scanner 86 acquires scan data representing the patient. The medical scanner 86 is configured by settings, such as a preset and/or user controlled settings, to scan the patient. The scan is a volume scan, such as scanning a three-dimensionally distributed region. The scan data may represent a volume of the patient. The medical scanner provides scan data representing locations distributed in three dimensions.

In alternative embodiments, the medical scanner 86 is not provided, but previously acquired scan data for a patient is stored in the memory 82. In yet other alternatives, many medical images are provided in the memory 82 as the training data, which is gathered and stored in the memory 82 from the medical scanner 86 or other sources.

The GPU 80 is a renderer, such as a graphics card, graphic chip, multi-core processor, or other processor for running a software package that implements the photorealistic image generation functionality. The GPU 80 is configured by an application programming interface to render one or more images from the 3D scan data representing a patient. Using physically-based rendering, a photorealistic image is rendered. Path tracing based on a pseudo-random number sequence generated from a seed is used to model light scattering. Using the seed and other rendering parameter settings, path tracing is applied to render the image. Other types of rendering may be used. For machine learning, the GPU 80 may render training images.

In one embodiment, the GPU 80 is configured to three-dimensionally render images from the scan of the volume of a patient or multiple patients. The images are rendered with different values for rendering parameters with a same seed (e.g., optimization selected seed). In other embodiments, the same values for the rendering parameters are used, but different RNG seeds are used in the rendering using a limited number of samples. In yet other embodiments, both the seeds and one or more other rendering parameters are changed for different images.

The image processor 88 is a computer, workstation, server, processor, or other device configured to apply machine learning, to apply a machine-learnt model, to select an image using optimization, and/or to optimize a RNG seed. The image processor 88 is configured by software, hardware, and/or firmware. For learning, the image processor 88 is configured by one or more machine learning algorithms. For applying a learnt model, the image processor 88 is configured, in part, by a learnt matrix or matrices associating input data to output values.

The image processor 88 applies a machine-learnt model, such as one learnt with deep learning. The image processor 88 is configured to search for one of the images matching a reference image based on a machine-learnt neural network, such as a representation network. The machine-learnt model, as implemented by the image processor 88, generates representation vectors from a reference image. The image processor 88 is configured to select an image and/or rendering parameters sufficiently similar (e.g., threshold) to the reference or best matching from a distance between representation vectors for the images and the reference. Optimization by the image processor 88 may be used to control the rendering settings used.

In another embodiment, the image processor 88 measures an error from renderings with different seeds to a reference image. An optimized seed is determined from the error, such as based on the number of samples providing sufficiently similar to a reference (e.g., threshold applied to the error) or the seed providing a best match (e.g., least error).

The memory 82 is a graphics processing memory, a video random access memory, a random-access memory, system memory, cache memory, hard drive, optical media, magnetic media, flash drive, buffer, database, combinations thereof, or other now known or later developed memory device for storing training data, rendering parameters values, one or more seeds, medical datasets, scan data, rendered images, error values, scalar values, and/or other information. The memory 82 is part of the medical scanner 86, part of a computer associated with the GPU 80, part of a computer associated with the image processor 88, a database, part of another system, a picture archival memory, or a standalone device.

The memory 82 stores scan data representing one or more patients. For example, data from the medical scanner 86 is stored. The data is in a scan format or reconstructed to a volume or three-dimensional grid format. The scan data is stored for training and/or stored for rendering an image or images of a patient.

The memory 82 or other memory is alternatively or additionally a non-transitory computer readable storage medium storing data representing instructions executable by the programmed GPU 80 and/or image processor 88 for learning or applying the machine-learnt model, for selecting a similar image, and/or for identifying a seed. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 84 is a monitor, LCD, projector, plasma display, CRT, printer, or other now known or later developed device for displaying the rendered image or images (e.g., photorealistic image or images). The displayed image or images may be of a volume of a patient. The display 84 receives images from the GPU 80, memory 82, image processor 88, or medical scanner 86. The images of the tissue captured by the medical scanner 86 are displayed. Other information may be displayed as well, such as generated graphics, text, or quantities as a virtual overlay.

Additional images may be displayed. For example, an image is rendered with physically-based rendering. An initial image is displayed. As further samples per pixel are performed in path tracing, the image is updated (e.g., one or more pixel colors are replaced with new colors or the entire image is replaced).

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for three-dimensional rendering in a rendering system, the method comprising:
   three-dimensionally rendering a reference image with path tracing using a first number of samples per pixel and a first random number generator seed;
   three-dimensionally rendering other images with the path tracing using different ones of other random number generator seeds, the three-dimensionally rendering for each of the other images using a second number or less than the second number of samples per pixel, the second number less than the first number by at least a factor of ten;
   measuring errors between each of the other images and the reference image;
   identifying one of the other random number generator seeds with a lessor error of the errors than the others of the other random number generator seeds; and
   configuring the rendering system for the path tracing with the identified one of the other random number generator seeds.

2. The method of claim 1 further comprising scanning a patient with a medical imaging system, and three-dimensionally rendering, by the rendering system as configured, an image from output of the scanning with the path tracing using the second number or less than the second number of the samples per pixel and the identified one of the other random number generator seeds.

3. The method of claim 2 further comprising performing the measuring and identifying as part of the three-dimensionally rendering of the image by the rendering system as configured being performed as interactive rendering from the output of the scanning.

4. The method of claim 1 wherein measuring the errors comprises measuring a number of the samples per pixel where the error reaches a threshold.

5. The method of claim 1 wherein three-dimensionally rendering the other images comprises emulating coherent scattering.

6. The method of claim 1 further comprising further rendering additional images as training renderings using the identified one of the other random number generator seeds, and training a neural network with deep learning to identify similar images with an architecture using a representation network connected to a decision network, the deep learning using the training renderings generated with the identified one of the other random number generator seeds.

* * * * *